United States Patent [19]

Krieg, Jr.

[11] Patent Number: 4,515,751

[45] Date of Patent: May 7, 1985

[54] MOISTURE CONTENT AND GAS SAMPLING DEVICE

[75] Inventor: Herman C. Krieg, Jr., Rancho Palos Verdes, Calif.

[73] Assignee: The United States of America as represented by the United States National Aeronautics and Space Administration, Washington, D.C.

[21] Appl. No.: 350,471

[22] Filed: Feb. 19, 1982

[51] Int. Cl.³ .............................................. G01J 1/50
[52] U.S. Cl. .................................... 422/86; 422/103; 422/88; 436/2; 73/40.7; 73/863.86; 73/864.52
[58] Field of Search ............... 422/86, 88, 103; 436/2, 436/39, 187, 169; 73/40.7, 863.86, 863.85, 864.52

[56] References Cited

U.S. PATENT DOCUMENTS

| | | | |
|---|---|---|---|
| 2,429,694 | 10/1947 | King | 73/29 |
| 3,399,973 | 9/1968 | Grosskopf | 422/60 |
| 3,429,186 | 2/1969 | Price et al. | 73/421.5 |
| 3,539,302 | 11/1970 | Dreckmann | 422/86 |
| 3,903,745 | 9/1975 | Bolser | 73/863.21 |
| 4,173,895 | 11/1979 | Pecor | 73/864 |

Primary Examiner—Hiram H. Bernstein

[57] ABSTRACT

An apparatus and method for measuring minute quantities of moisture and other contaminants within sealed enclosures such as electronic assemblies which may be subject to large external atmospheric pressure variations.

An array of vacuum quality valves (20 thru 32) is arranged to permit cleansing of the test apparatus of residual atmospheric components from a vacuum source (13). This purging operation evacuates a gas sample bottle (36), which is then connected by valve settings to provide the drive for withdrawing a gas sample from the sealed enclosure under test into the sample bottle through a colometric detector tube (Drager tube) (19) which indicates moisture content. The sample bottle (36) may be disconnected and its contents (drawn from the test enclosure) separately subjected to mass spectrograph analysis. The use of an inert reference gas (12) admitted during the test, facilitates the determination of free volume and internal pressure within the test unit.

11 Claims, 4 Drawing Figures

MOISTURE CONTENT AND GAS SAMPLING DEVICE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; U.S.C. 2457).

TECHNICAL FIELD

My invention relates generally to systems and methods for determining the acceptability of sealed enclosures, by performing insitu measurement of the physical properties of the internal pressurant, (i.e. internal pressure, gaseous volume and gas composition) and comparing these data to known standards and/or requirements. The invention was initially developed to perform field inspection of hermetically sealed electronic devices wherein the major task was to validate the unit's internal and external mechanical seals and in addition to determine the presence of (and the amount of, if present) moisture within the device.

BACKGROUND ART

Certain electronic devices are susceptible to damage and accelerated degradation when exposed to chemical constituents found in normal atmospheric air. One of the principal offending chemical compounds but, not the only compound, is water; usually present in the vapor phase. For this reason critical electronic circuits are either incapsulated in isolation material or placed in special containers which are either evacuated to a high vacuum (i.e. vacuum tubes) or pressurized to various levels with dry inert gases (nitrogen, for example), after which the sealed, or isolated, components are placed in a mechanical enclosure, which itself is sealed and pressurized with a similar or different inert gas.

A major problem exists since all mechanical seals have a tendency to leak, and in addition if elastomers are used as the sealing surfaces, gaseous permeation through the elastomic seals will occur. Contamination of the dry inert gas is not only possible, but unavoidable. This is particularly true when the electronic assembly forms part of a space vehicle which is designed to be recovered and recycled (Space Shuttle, for example). Water vapor and other contaminants will permeate through the elastomeric seals at the access parts and/or flanges and eventually will affect the critical components when the contaminants exceed critical threshold levels. Such contamination is subsequently deposited and/or absorbed on internal surfaces and/or electronic components within the enclosure and can be the cause of malfunction or outright failure.

The purging and repressurizing of a sealed electronic enclosure may not dispose of the accumulated water vapor to a high degree. In fact it usually only removes that portion of the water vapor present in the gas; the major portion of the moisture present in the unit would be absorbed within the unit's internal constituents. Complete removal of moisture contained in the device would require thermal bake out under a high vacuum. Accordingly, objective evidence of the readiness of a sealed electronic unit requires a field test apparatus and procedure.

Colometric analysis, which is employed in the novel combination of the invention, is known per se for qualitative and quantitative analysis. In-line detector tubes may be procured commercially or may be specially prepared for detection of specific gases and vapors. One such detector comprises an elongated transparent tube containing a chemical material through which gas may be passed. In the absence of water vapor in the gas, the chemical material is yellow in color. As gas is passed through the tube, however, any water vapor present is absorbed from the input end and on along the tube so that a red color replaces the initial yellow of the chemical material for a distance along the tube proportional to the amount of water absorbed. Such devices are manufactured by Dragerwerk of Lubeck, Germany, and are sometimes called Drager tubes.

U.S. Pat. No. 2,429,694 describes several forms of colometric tubes involving water induced color change in a particulate material through which water-containing gas is passed.

Prior to the invention, no adequate means of performing the desired measurements existed. In fact, conventional gas sampling with subsequent analysis (by mass spectrography, for example), usually compromised the accuracy, or overlooked entirely, the water vapor constituent, because the minute quantities present were absorbed on the sample bottles' interior surfaces. Attempts to reclaim the water vapor constituent usually yielded mixed results because of uncertainty as to the bottles' initial condition.

In the prior art, gas sampling systems and components are variously described in the patent literature.

U.S. Pat. No. 3,903,745 discloses a gas sampling device for collecting and measuring gaseous emission components from flues, but does not address quantitative water vapor detection, although a moisture trap is suggested. Vacuum pumping and a sample collection vessel are shown.

U.S. Pat. No. 4,173,895 is concerned with liquid oxygen sampling and is of interest in that it shows a valve, manifold and pressure gauge arrangement.

U.S. Pat. No. 3,429,186 describes intermittent sampling of a gas flowing in a main, and U.S. Pat. No. 3,539,302 provides a color sensitive material for trace gas detection.

None of the foregoing patents shows or suggests the apparatus or purpose of the invention.

The so-called Drager tube detector which has been incorporated in the novel combination to be described is basically disclosed in U.S. Pat. No. 3,399,973.

DISCLOSURE OF THE INVENTION

The objective of this invention is to provide a field usable apparatus capable of determining by qualitative and quantitative means the physical characteristics (i.e.: pressure, void volume and amount of contaminant such as water vapor) of the gas contained within a sealed electronic enclosure.

By comparison of these measured parameter against known standards or previously measured values, the acceptability or rejectability of the electron unit for flight operation may be determined.

The invention comprises a unique combination of a vacuum tight apparatus for analyzing the gas contained within a sealed enclosure, an electronic apparatus for example. The invented apparatus is referred to as the MAGS (Moisture And Gas Sampling) device. The major components of the MAGS combination include a coupling or interface device permitting connection to the enclosure, the latter having, for example, a Schrader valve which is activated to admit gas into the closed interior of the coupling device. An impedance device within the coupling device slows gas passage to an output joining a capillary tube feeding an upper manifold. A Drager tube for detecting water in the gas feeds from the upper manifold to a similar lower manifold and thence to a sample bottle. An absolute pressure gauge is connected to the upper manifold and another to the lower manifold. The "plumbing" interconnections are made through a network of vacuum-tight valves so that all portions of the apparatus may be cleansed by opening certain of the valves to a vacuum source. A calibrated sample bottle is thus evacuated and becomes a negative pressure source for extracting a gas sample into itself. The manifolds are of minimal volume, each comprising essentially only the volume within the tubing fittings formed into a cross.

An arrangement for admitting a reference gas into the apparatus facilitates, along with pressure and temperature measurements (at the sample bottle, the electronic enclosures and the manifolds), the collection of data makes possible the calculation of enclosure's internal gas pressure and free volume (void) therein.

The sample bottle is disconnected for subsequent further analysis, by mass spectrograph, for example.

BRIEF DESCRIPTION OF DRAWINGS

The details of the invention are presented in connection with the accompanying drawings, in which.

BEST MODE FOR CARRYING OUT THE INVENTION

Figure 1:
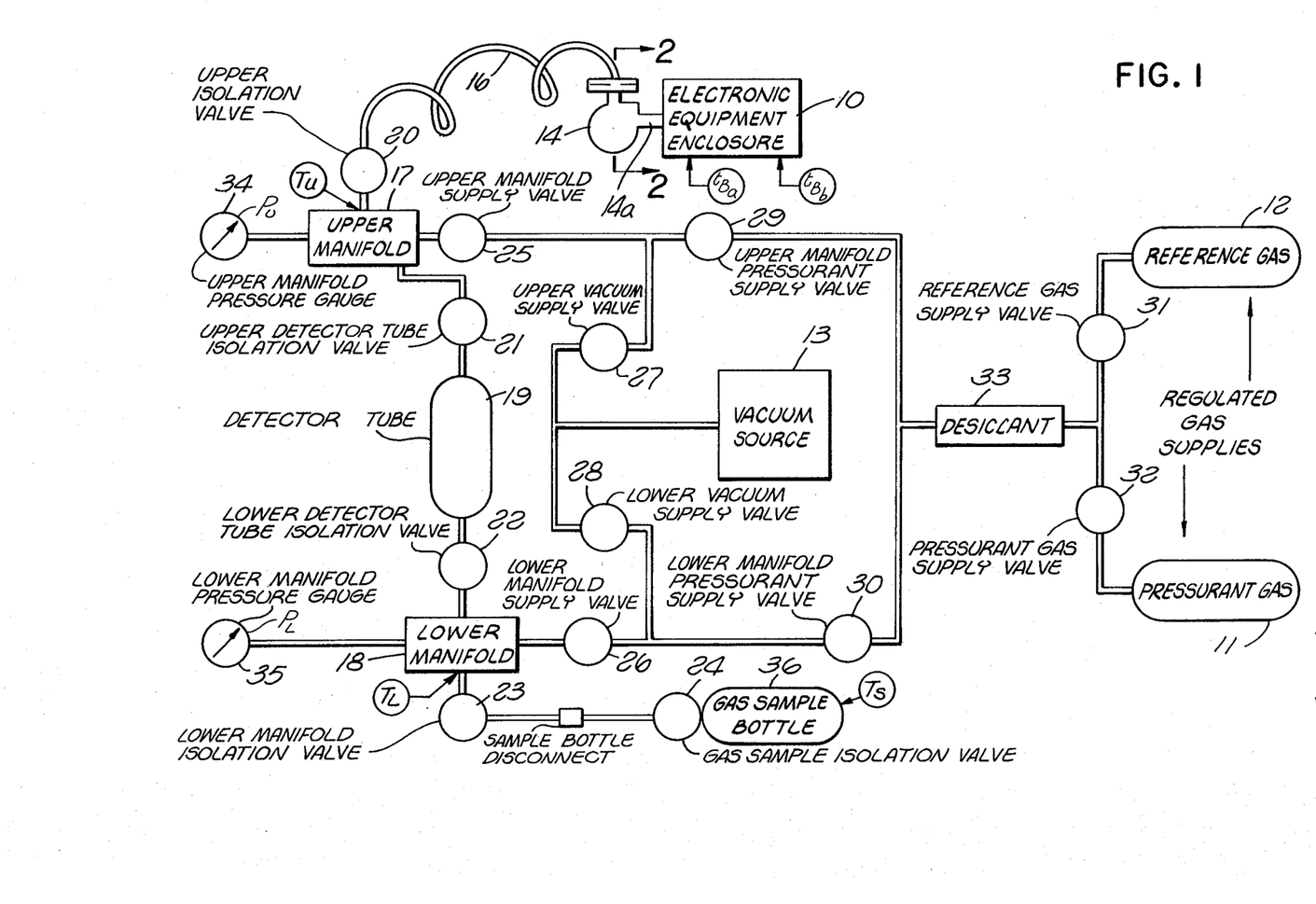
FIG. 1 is a schematic layout showing the interconnection of the components of the apparatus of the invention.

Referring now to FIG. 1, the apparatus of the invention is best explained by combining an operational description with it.

It will be noted from FIG. 1, that two gas supplies (having conventional regulators) are included. One of these is the pressurant gas 11 used to recharge the electronic enclosure under test after the test procedure is completed. Gas supply 11 must meet the specification for the original pressurant used in the electronic enclosure.

The second gas supply 12 is an inert reference gas which is not a component of the pressurant gas, but is a trace constituent of the atmosphere in which the electronic device normally functions. Argon, neon and/or krypton, the so-called noble gases make suitable reference gases. Helium and nitrogen, on the other hand, would not be satisfactory reference gases since they are normally major constituents in the enclosure pressurant gas and could not be called trace atmospheric constituents.

The vacuum source 13 may be obtained by any conventional means, (i.e. vacuum pump, aspirated supply and/or a large evacuated tank. When activated while in the MAGS apparatus, the vacuum source 13 should produce a vacuum of approximately between 2 to 500 torr absolute pressure.)

The sole function of the vacuum source is to provide a means to evaluate and cleanse the internal volumes of the MAGS device of any residual gases from the atmospheric environment.

Figure 2:
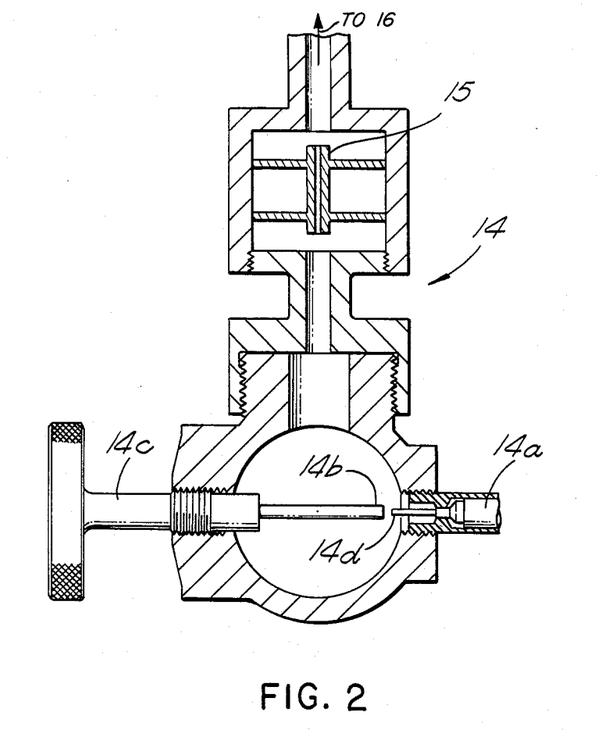
FIG. 2 is a detail of the coupling device for interfacing the test apparatus and the enclosure subject to test.

The major components of the MAGS apparatus consist of a coupling or interface device 14 which includes an impedance device 15 (see FIG. 2), upper and lower manifolds 17 and 18, trace gas detector tube 19 and the sample collection bottle 36. A functional description of these components follow:

The coupling 14 provides a means for connecting the MAGS test kit to the electronic equipment enclosure under test. Usually the electronic equipment enclosure connection is made to a Schrader fill valve 14a actuator which in turn is attached to the enclosure's fill valve (FIG. 2).

Immediately adjacent and within the body of the connector 14 is the impedance device 15. As the name implies, the impedance device retards the gaseous diffusion process between the gases upstream of the device 15 and those downstream of it. Given ample time, two different volumes of gas, each with different constituents will equalize once interconnected. The equalization process is controlled by the diffusion rates of the respective gases. The impedance device tends to reduce the transfer rates; thus forming a temporary barrier within the time span needed to complete the MAGS test.

The impedance device 15 is attached to a capillary tube 16, which provides the flow path to the upper and lower manifolds, 17 and 18, respectively.

The upper manifold 17 and the lower manifold 18 provide a means for attaching and directing the flow of gases between the various components and/or gas supplies within the system.

In addition they provide a means for attaching the pressure gauges 34 and 35 and temperature measurement probes TU and TL. Gas flows from the upper manifold to the lower manifold through a detector tube 19 as long as valves 25 and 26 are closed and valves 21 and 22 are open and the lower manifold is at a lower pressure.

Figure 3:
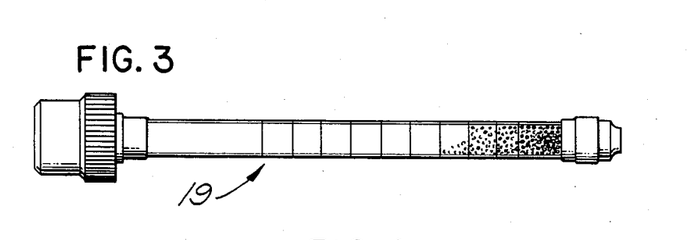
FIG. 3 illustrates a typical detector (Drager) tube of FIG. 1.

The detector tube 19 is a calibrated device which can measure the trace quantities of a selected constitutent within a gas as it passes through the tube. In the conventional apparatus described herein, the trace constituent is water vapor and the detection method is characterized as colormetric.

The gas is drawn through the detector tube 19 and lower manifold 18 into a large pre-evacuated gas sample bottle 36. The gas sample bottle serves a dual function; initially it is a large reservoir at low pressure thus providing a necessary driving force to draw the gas through the system, and second it provides the means of transporting the collected gas sample to an analytical laboratory for further evaluation of the major gas constituents after closing valve 24 and separation of the disconnect joint.

To provide control and isolation between the various components and gas supplies, a number of hand operated control valves are provided. A description and function of the 13 control valves is provided in the following table:

TABLE 1

| VALVE | NAME | FUNCTION |
|---|---|---|
| 20 | Upper Isolation Valve | Provides primary isolation between the electronic test unit and the |

TABLE 1-continued

| VALVE | NAME | FUNCTION |
|---|---|---|
| 21 | Upper Detector Tube Isolation Valve | upper manifold. Provides isolation between the upper manifold and the detector tube inlet. |
| 22 | Lower Detector Tube Isolation Valve | Provides isolation between the outlet tube and the entrance to the lower manifold. |
| 23 | Lower Isolation Valve | Provides redundant isolation between lower manifold and the gas sample bottle, thus enabling removal of gas sample bottle. |
| 24 | Gas Sample Isolation Valve | Provides primary isolation and containment of the gas sample within gas sample bottle |
| 25 | Upper Manifold Main Supply Valve | Provides redundant main control and isolation between the regulated pressure supplies, vacuum source and the upper manifold. |
| 26 | Lower Manifold Main Supply Valve | Provides redundant main control and isolation between the regulated pressure supplies vacuum source and the lower manifold. |
| 27 | Upper Manifold Vacuum | Provides isolation and control between the upper manifold and the vacuum source. |
| 28 | Lower Manifold Vacuum | Provides isolation and control between the lower manifold and the vacuum source. |
| 29 | Upper Manifold Pressurant Supply Valve | Provides isolation and control between the upper manifold and regulated gas supplies |
| 30 | Lower Manifold Pressurant Supply Valve | Provides isolation and control between the lower manifold and regulated gas supplies |
| 31 | Reference Gas Supply Valve | Provides isolation and control between the MAGS and the reference gas supply |
| 32 | Pressurant Gas Supply Valve | Provides isolation and control between the MAGS and the pressurant supply |

As a precaution against introducing contaminant moisture into the system, a desiccant tube 33 is provided between the pressurant supply valves and the regulated gas supplies. The function is to remove any trace of moisture in the gas supplies.

System pressures are measured by two high resolution absolute pressure gauges, 34 and 35, which are connected to the upper and lower manifolds 17 and 18, respectively.

Five (5) system temperature measurement probes (i.e. thermocouples) are required as shown in FIG. 1.

| Thermocouple $t_{Ba}$ | Applied to the electronic equipment enclosure under test at a location "a" to measure the highest expected temperature |
|---|---|
| Thermocouple $t_{Bb}$ | Applied to the electronic equipment enclosure under test at a location "b" to measure the lowest expected temperature. |

The function of Thermocouple $t_{Ba}$ and Thermocouple $t_{Bb}$ is to provide an average mean temperature $t_B$ for the devices under test by averaging their separate readings.

| Thermocouple $T_u$ | Applied to the center of the upper manifold 17. The function is to provide a measurement of the upper manifold temperature. |
|---|---|
| Thermocouple $T_L$ | Applied to the center of the lower manifold 18. The function is to provide a measurement of the lower manifold temperature manifold. |
| Thermocouple $T_s$ | Applied to the outer skin of the gas sample bottle near its mid-girth. |

To determine the internal pressure and moisture content of the gas within a sealed pressurized electronic device, a MAGS test is performed according to a test procedure, obtaining readings as indicated.

PROCEDURE

The preferred procedure for operating the apparatus of the invention is as follows:

1. The interface device 14 is connected to the Schrader valve 14a attached to the electronic equipment enclosure, with the activating plunger 14b in the withdrawn position as viewed in FIG. 2.
2. Close all valves 20 through 32.
3. Open valves 25 through 28.
4. Connect and energize vacuum source 13 absolute pressure gauges 34 and 35 and regulated gas supplies 11 and 12. The scale ranges of gauges 34 and 35 should be 2 and 1 atmospheres, respectively.
5. Install Drager tube 19 by scoring and breaking off the glass end seals and coupling to attachment couplings connectable to MAGS plumbing as indicated in FIG. 1.
6. Attach a calibrated gas sample bottle 36 to lower manifold 18, and record the internal volume of bottle 36 for use in subsequent calculations.
7. Evacuate the MAGS test system by opening valves 20, 22 through 24, and 29 and 30. Valves 21, 31 and 32 remain closed at this time.
8. Note and record system pressures on gauges 34 and 35 after achievement of steady state readings. Both gauges should indicate the same pressure within one torr.
9. Close valves 27 and 28, isolating vacuum source 13, and monitor gauges 34 and 35 to verify that vacuum is maintained in the MAGS "plumbing". Record the pressures. Increasing pressure indicates leakage, which must be remedied before proceeding. Valves 22, 25 and 26 may be temporarily closed for leak isolation but must be reopened prior to continuation of the procedure.

After the vacuum integrity of the system has been verified, the system is now cleared of extraneous air by purging with the reference gas as follows.

10. Slowly open valve 31 and activate regulator on reference (argon) gas supply 12 to pressurize system with reference gas to a specified pressure value P(R) above the system vacuum by 200 to 500 torr.
11. Close valves 29 and 31 and deactivate reference gas regulator.
12. Evacuate MAGS system by opening valves 27 and 28.
13. Note and record steady state pressure readings of gauges 34 and 35.

14. Close valves 27 and 28 and monitor gauges 34 and 35 for approximately one minute to verify that vacuum is maintained (i.e. system shall not gain more than 1 torr). Record pressure.

15. Close valves 26 and 30. This isolates the lower section, leaving it in a vacuum condition.

16. Open valve 29 and then slowly open valve 31 and again activate reference gas regulator to pressurize system with reference (argon) gas until previously indicated pressure P(E) is reached.

17. Close valves 25, 29 and 31 and deactivate ref. (argon) gas regulator.

18. Note and record gauge pressures and verify that gauge 35 does not show increase of pressure in excess of one torr.

19. Record all thermocouple (temperature) readings. The test system is now ready for communication with the electronic equipment enclosure gas.

20. Open Schrader valve 14a by rotating valve handle 14c to depress 14d. Pressure equalization between the test electronic equipment enclosure and the upper manifold 17 will now occur.

21. Record all temperature ($t_{Ea}$, $t_{Eb}$, $T_u$, $T_L$ and $T_s$) and pressure at gauges 34 ($P_u$) and 35 ($P_L$).

22. Slowly open valve 21. This allows gas to flow through the detector tube 19, into the lower manifold system. Gas flow continues until the pressures in the upper and lower manifolds are equal.

23. Observe the indicated pressures on the upper and lower manifold pressure gauges (34 and 35).

24. When equilibrium is reached, record all temperatures ($t_{Ea}$, $t_{Eb}$, $T_u$, $T_L$ and $T_S$) and pressure at gauges 34 ($P_u$) and 35 ($P_L$).

25. Close valves 20, 21, 22, 23, and 24.

26. Remove Drager tube 19 and record the indicated level of water vapor (Drager tube reading should be taken before water vapor in the air can alter humidity reading).

27. Remove gas sample bottle 36 by dismantling connection between valves 23 and 24 and forward bottle 36 for further analysis promptly. This gas is available for constituent identification and quantitative determination of the collected gas.

28. If electronic enclosure is to be refilled with fresh pressurant gas, evacuate MAGS and test unit by opening valves 20, 25 and 27, and when pressure stabilization occurs, close valve 27.

29. Pressurize test unit by slowly opening valves 29 and 32, adjusting the Pressurant Gas regulator to P(F) which is the pressure selected for flight, plus approximately 0.5 psia.

30. Close valves 29 and 32 after pressures equalize and deactivate pressurant gas regulator on supply 11.

31. To prevent contamination of electronic enclosure from MAGS test repeat evacuation and repressurization steps 28 through 30.

32. Close Shrader Valve 14a by rotation of 14c to withdraw plunger 14b.

MAGS assembly may now be disassembled.

The actual computation of the unknown properties, such as initial internal gas pressure, contaminant (i.e. water vapor) concentration and the void volume, is based on the Ideal gas law, the calibrated volume and the measured physical conditions (i.e. pressure and temperature).

MATHEMATICAL ANALYSIS

Figure 4:
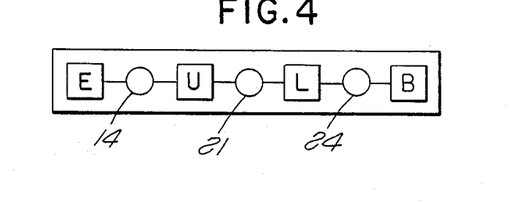
FIG. 4 is a block diagram of four key sections of the MAGS necessary for mathematical analysis.

For simplicity, refer to FIG. 4 showing blocks E, followed by U, followed by L, followed by B.

Block E represents the electronic equipment enclosure under test, and includes the volume and/or gas up to the Valve seat in the unit's fill valve 14a, (FIG. 1).

Block U refers to that volume and/or gas between valve seats, of the fill valve 14a, the upper pressurant-/vacuum isolation valve 25, and the upper detector valve 21, including that volume and/or gas contained in the upper Pressure gauge 34 (FIG. 1).

Block L refers to that volume and/or gas between the valve seats of the upper detector tube valve 21, the lower pressurant/vacuum inlet (lower manifold supply) valve 26 and the bottle 19 isolation valve 24, including that volume and/or gas in the detector tube 19, and the lower pressure gauge 35 (FIG. 1).

Block B refers to that volume and/or gas contained in the calibrated sample bottle 36 downstream of the isolation valve 24 (FIG. 1).

From the ideal gas law, at any instant, the weight, W, of gas contained in any block is $$W = PVM/rt$$

where
P = Pressure
V = Volume
M = Molecular Weight
T = Absolute Temperature
r = Gas constant.

Subscripts E, U, L, and B will be used to refer to one of the aforementioned blocks. Subscripts 1 and 2 will refer to pre and post states respectively, and subscript R will refer to the inert reference gas used in the flushing and purging operations.

DETERMINATION OF INITIAL PRESSURE

The internal pressure of the subject unit may be calculated from the data collected by the procedure. Initially the total mass of gas, $W_S$, contained in Blocks E and U after charging the upper manifold with the Reference Gas R, is:

$$W_{S1} = W_{E1} + W_{U1} \tag{2}$$

and following actuation of the fill valve 14a, the total system weight is:

$$W_{S2} = W_{E2} + W_{U2}. \tag{3}$$

Since no gas is lost, only redistributed between the blocks, $$W_{E1} + W_{U1} = W_{E2} + W_{U2}. \tag{4a}$$

Also, $$M_{U1} = M_R \tag{4b}$$

Using the ideal gas law equation (4) may be expressed as:

$$\frac{P_{E1} V_E M_{E1}}{r T_{E1}} + \frac{P_{U1} V_U M_R}{r T_{U1}} = \frac{P_{E2} V_E M_{E2}}{r T_{E2}} + \frac{P_{U2} V_U M_{U2}}{r T_{U2}} \tag{5}$$

Note that $M_R$ (the molecular weight of the reference gas)=$M_{U1}$, since region U is initially only reference gas.

After fill valve actuation, the pressure in each block equalizes such that:

$$P_{E2} = P_{U2} = P_S = \text{Pressure in blocks E and U} \quad (6a)$$

and considering the relatively small mass of the gas, compared to the mass of the system, the block temperatures are essentially constant such that we can assume:

$$T_{E1} = T_{E2} = T_E \quad (6b)$$

and that $$T_{U1} = T_{U2} = T_U. \quad (6c)$$

On Substituting equations (6a), (6b), and (6c) in equation (5) and solving for $P_{E1}$:

$$P_{E1} = P_S \frac{M_{E2}}{M_{E1}} + \frac{V_U T_E}{V_B T_U M_{E1}} (P_S M_{U2} - P_{U1} M_{R1}) \quad (7)$$

Only three cases are possible, as follows:
(1) $P_{U2} > P_{U1}$
(2) $P_{U2} = P_{U1}$
(3) $P_{U2} < P_{U1}$ The next section will show that in all cases the same relationship evolves:

$$P_{E1} = P_{U2} + \Delta P_U \left( \frac{V_U T_E}{V_E T_U} \right) \quad (8)$$

Considering each of these cases separately:
CASE 1, if
$P_{U2} > P_{U1}$, then gas flowed into U from E, therefore:

$$M_{E2} = M_{E1} \quad (9a)$$

and $$M_{U2} = M_{fE} M_{E1} + mf_R M_R. \quad (9b)$$

Where $mf_E$ is the mole fraction of gas from Block E and $mf_R$ is the mole fraction of the reference gas under the new pressure.

Since the mole fractions may be represented by the sum of the partial pressure ratios, equation 9b may be written as $$M_{U2} = \frac{P_{U2} - P_{U1}}{P_{U2}} M_{E1} + \frac{P_{U1}}{P_{U2}} M_R \quad (9c)$$

where $$P_{U2} - P_{U1} = \Delta P_U \quad (9d)$$

After substitution equation 7 becomes:

$$P_{E1} = P_{U2} + \Delta P_U \left( \frac{V_U T_{E1}}{V_E T_{U2}} \right) \quad (9e)$$

Notice similarity to equation 8.

CASE 2, if
$P_{U2} = P_{U1} = P_s$ equals the pressure in blocks E and U;
Then no gas has flowed across the interface, therefore:

$$M_{E2} = M_{E1} \quad (10a)$$

$$T_{E2} = T_E \quad (10b)$$

$$M_{U2} = M_R \quad (10c)$$

$$T_{U2} = T_U \quad (10d)$$

and, $$P_{E1} = P_{U2} + P_{U2} \left( \frac{V_U}{V_E} \frac{M_{U1}}{M_{E1}} \frac{T_E}{T_U} \right) - P_{U1} \left( \frac{V_U}{V_E} \frac{M_{U1}}{M_{E1}} \frac{T_E}{T_U} \right) \quad (10e)$$

After substitution into equation 7, and clearing, $$P_{E1} = P_{U2} + (\Delta P_U) \left( \frac{V_U}{V_E} \frac{T_E}{T_U} \right). \quad (10f)$$

Notice similarity to equation 8.

CASE 3, if
$P_{U2} < P_{U1}$ Where some gas flows from Block U into Block E, therefore:

$$M_{U2} = M_{U1} \quad (11a)$$

$$T_{U2} = T_U \quad (11b)$$

similarly $$M_{E2} = mf_E M_{E1} + mf_R M_{U1}. \quad (11c)$$

The number of moles of reference gas from Block U in Block E, $n_{UE}$, is $$n_{UE} = \frac{(P_{U1} - P_{U2}) V_U}{r T_U} \quad (11d)$$

since $PV = nrT$ (Ideal Gas Law), the volume of the reference gas passing into E, $V_{RE}$, is $$V_{RE} = V_U \left( \frac{P_{U1} - P_{U2}}{P_{U2}} \right) \frac{T_E}{T_U} \quad (11e)$$

Since the volume ratio is equal to the pressure ratio, $$mf_{RE} = \frac{V_{RE}}{V_E} = \frac{V_U}{V_E} \left( \frac{P_{U1} - P_{U2}}{P_{U2}} \right) \frac{T_E}{T_U} \quad (11f)$$

Substituting in equation 7 and clearing, $$P_{E1} = P_{U2} + \Delta P_U \left( \frac{V_U T_E}{V_B T_U} \right) \qquad (11g)$$

Notice similarity to equation 8.

Conclusion

It has thus been shown that each of the three cases may be reduced to an identical expression.

The initial internal pressure of the device under test, therefore, is dependent upon its internal freevoid volume in test article 10, the internal volume of the upper manifold 17 and the measured pressures before and after equalization. A slight correction for the actual temperature levels in the various locations may be applied for greatest accuracy.

Design Consideration

For a practical test device, the volume of the upper manifold 17 is minimized (usually in the order of 10 cc's or less) by the use of capillary tubing and minimum length connections between supporting components.

At the same time the internal void volume of the electronic device is usually relatively large, normally in excess of 1,000 cc's. Thus the volume ratio is on the order of 0.01 or less. If at the same time the observed change in pressure before and after equalization is also small, for all field applications, the correction term, $P_U(V_U)/(V_B)(T_B)/(T_U)$, may be ignored. The final equilibrium pressure may therefore be considered to be the actual internal pressure of the test device.

If the actual volumes are known the correction term may be utilized for improved accuracy.

DETERMINATION OF CONTAMINATE (WATER VAPOR) CONCENTRATION

The moisture content of the gas in the test article may be determined as follows:

Subsequent to the actuation of the Schrader valve 14a and the equalization of pressures within the upper manifold 17 and the test article 10 according to the procedure and recording of necessary pressures and temperatures in E and U, the upper detector tube isolation valve 21 is opened allowing gas to flow through the detector tube 19 and into the lower manifold 18, and the gas sample bottle 36, all of which were pumped down to a vacuum by source 13.

As the gas passes through the detector tube 19, moisture is chemically removed from the gas. The chemical reaction causes a colormetric change, from yellow to red, to occur. The color change is progressive and proceeds in a systematic manner. That is, the amount of material which changes color is directly proportional to the amount of water reacted. By physically measuring the amount of material which reacted (i.e. the length of the red zone) and comparing that amount (length) to a precalibrated standard, the precise amount of moisture absorbed by the tube, $W_{WDT}$, may be calculated.

The amount of gas which was drawn through the detector tube can be determined by means of the ideal gas laws.

Prior to emptying the electronic equipment enclosure, the gas sample bottle 36 and the lower manifold 18 contained a pure reference gas, typically argon, at vacuum conditions.

The weight of reference gas initially present in the lower system, $W_{RL-B}$ equals that in the lower manifold, $W_{RL}$, and that in the sample bottle, $W_{RB}$ $$W_{RL-B} = W_{RL} + W_{RB} \qquad (12)$$

$$= \frac{P_{L-B} V_L M_R}{r T_L} + \frac{P_V V_B M_R}{r T_B}$$

Where $P_{L-B}$ = Pressure in lower system prior to opening valve 32.
$V_B$ = Volume of gas sample bottle 36.
$V_L$ = Volume of lower manifold 18.
$M_R$ = Molecular weight of reference gas.
$T_B$ = Temperature of gas sample bottle.
$T_L$ = Temperature of lower manifold.
$r$ = Gas constant.

Following actuation of Valve 21, and after the pressures equalize between the upper and lower system the weight of gas, $W_{gL-B}$ in the lower system is $$W_{gL-B} = W_{gL} + W_{gS} \qquad (13)$$

where
$W_{gL}$ = Weight of gas in lower manifold
$W_{gB}$ = Weight of gas in gas sample bottle Using the ideal gas law $$W_{gL-B} = \frac{P_{L-B} V_L M_G}{r T_L} \quad \frac{P_{L-B} V_B M_G}{r T_B} \qquad (14)$$

where $M_G$ is the average molecular weight of the gas in the lower system L and B.

For a preliminary estimate the average molecular weight may be assumed to be the average between the composition of the pressurant at the initial filling and the composition of the ambient atmosphere to which the box was exposed. In the final calculation, the actual gas composition is known, (since a standard mass spectrographic analysis is performed as part of the procedure) and the actual average molecular weight can be calculated. In either case the amount of gas which flowed through the detector tube, $W_{gDT}$, is the difference between the final and initial values.

This information when combined with the total weight of water absorbed in the detector tube, $W_{WDT}$, yields a precise determination of the moisture content in the original electronic equipment enclosure.

VOID VOLUME DETERMINATION

The void volume of the electronic equipment enclosure may now be computed, since $$W_E = W_{EL} + W_{EO}$$

where $W_E$ is the weight of gas originally in the test article, $W_{EL}$ is the weight of gas left in the electronic equipment enclosure at the completion of the test and $W_{EO}$ is the weight of gas that flowed out of the electronic equipment enclosure including the weight of gas in the upper manifold and that gas which flowed through the detector tube.

Using the ideal gas law $$\frac{P_E V_E M_E}{r T_E} = \frac{P_{L-B} V_E M_E}{r T_E} + \qquad (15)$$

$$\frac{P_{L-B} V_U M_E}{r T_U} + W_{WDT} + W_{gDT}$$

but, restating equation 8, $$P_E = P_{U2} + P_U \frac{V_U}{V_E} \frac{T_E}{T_U}$$

Where $P_{FL-B}$ is the final pressure in the Lower Manifold after equalization.
therefore $$V_E = \left(\frac{P_{L-B} - P_U}{P_{U2} - P_{L-B}}\right) V_U \left(\frac{T_E}{T_U}\right) + \left(\frac{W_{WDT} + W_{GDT}}{P_{U2} - P_{L-B}}\right)\left(\frac{r T_E}{M_E}\right) \quad (16)$$

ILLUSTRATIVE EXAMPLE

The following paragraphs present an illustrative example, wherein the acceptability of a field unit will be evaluated using the methods and equations previously described.

In this particular example, the electronic device has been temperature conditioned for a period of twenty-four hours to assure that any moisture contained in the device will be driven into the vapor phase. When the electronic device was initially assembled, and sealed, it was pressurized to 16.0 psia at 75° F. (534.7° R), with an inert dry gas containing 10% by volume Helium and 90% by volume nitrogen. The "as assembled" void volume was measured to be 990 cc. An additional 200 cc of void volume was contained in an internal "sealed" and "evaluated" compartment, whose seals were subject to disintegration and failure.

Table 2, presented below summarizes measurements and data collected during the performance of the procedure described earlier. The reference gas used in the performance of this test was argon.

The initial pressure was determined based on the prior history of similar devices. (i.e. it was known that the seals in this particular device had a history of high leakage rates) and was accordingly biased on the low side.

The calculations are performed in two parts:

In Part 1, the initial results will be based on an estimated molecular weight for the gas in the sample bottle. The estimates are based on prior experience.

In Part 2, the final results will be based on refined test data and the results of a mass spectrometry analysis of the gas in the sample bottle.

TABLE 2
Illustrative Test Data Measurements (typical)

| | |
|---|---|
| Temperature | |
| $T_{Ea} =$ | 171.4° F. = 631.1° R. |
| $T_{Eb} =$ | 167.0° F. = 626.7° R. |
| $T_U =$ | 77.0° F. = 536.7° R. |
| $T_L =$ | 77.0° F. = 536.7° R. |
| $T_B =$ | 77.0° F. = 536.7° R. |
| Volumes (cc) | |
| $V_E =$ | To be determined. |
| $V_U =$ | 2.4 (manifold) + 14.0 (gauge) = 16.4 (total) |
| $V_L =$ | 3.7 (manifold) + 14.0 (gauge) = 17.7 (total) |
| $V_B =$ | 1016.0 |
| Pressures (Torr) | |
| Initial Pressure in Upper Manifold, $P_{U1,} =$ 812.33 | |
| Equalization pressure, $P_{U2}$, (immediately after step 20 of page 13) = 928.41. | |
| Initial Pressure in Lower Manifold, $P_{IL-B}$, (prior to step 22 of page 14) = 3.50. | |
| Final Pressure in Lower Manifold, $P_{FL-B'} =$ 410.00. | |
| Drager Tube Reading = 20.5 mg. H₂O | |

START OF SAMPLE ANALYSIS

Part 1

This phase of the analysis is usually performed in the field immediately upon collection of data. The intent of the analysis is to yield a go-no-go decision as to the acceptability of the unit.

INITIAL RESULTS (PRELIMINARY FIELD RESULTS)

Pressure Determination
$P_{U1} = 812.83$ Torr
$P_{U2} = 928.41$ Torr
$P_U = P_{U2} - P_{U1} = 115.57$ Torr The average temperature of the electronic device is determined by:

$$T_E = \frac{T_{Ea} + T_{Eb}}{2}$$

$$= \frac{631.1 + 626.7}{2}$$

$$= 629.4° R$$

$$T_U = 536.7° R$$

For a first cut approximation the volume, $V_B$, will be assumed to be in the order of the original measurement. Therefore set, $$V_E = 1000 \text{ cc}$$

$$P_E = P_{U2} + \Delta P_U \left(\frac{V_U}{V_E} \frac{T_E}{T_U}\right)$$

$$= 928.41 + 115.57 \left(\frac{16.4 \times 629.4}{1000 \times 536.7}\right)$$

$$= 928.41 + 2.22$$

$$= 930.63 \text{ Torr}$$

calculated pressure in electric device at the time of the test.

The actual pressure in the electronic device at the time of the test was 930.63 TORR. However, since the test unit was maintained at an average temperature of 169.76 degrees F., the measured value must be normalized to the original fill temperature, 75 degrees F., in order to compare this measured value with the original starting pressure, (original fill) pressure. This is accomplished by $$P_{E(75)} = P_{E(169.7)} \left( \frac{T_{FILL}°R}{T_E°R} \right)$$

$$= 930.63 \frac{(534.7)}{(629.4)}$$

$$= 790.61 \text{ Torr.}$$

which is equivalent to 15.28 psia.

Since this value is significantly below the original fill pressure, 16.0 psia, it is apparent that something has changed within the unit. There are only three possibilities.

(1) The external seals have become defective allowing gasses to escape.

(2) The internal seals on the isolated sections within the device have become defective allowing gases to enter the internal sealed off compartments.

(3) A combination of (1) and (2) above.

In any case the unit is suspect. If the integrity of the internal seals may be verified, the unit may be acceptable for limited usage, since the internal pressure is still slightly above the allowable lower limit (which in this case was 15.0 psia). This, of course, assumes that no moisture has permeated into the device.

Calculating the Moisture Content of the Internal Gases

The moisture content (in the form of water vapor) of the gases contained with the electronic device is calculated in the following manner.

(1) The total volumeric quantity of the gases contained in the lower manifold system $V_{GL-R}$ after final pressure equalization, i.e., step 24, is determined. This is possible since the absolute volume of the lower manifold system, with its sample bottle is known, and the average final temperature, $T_{SL-R}$ is measured. For convenience the quantities are expressed in terms of standard cubic centimeters, SCC. SCC is the volume that a given amount of gas will occupy at standard conditions of temperature and pressure, 32° F. (491.7° R) and 760 Torr respectively. SCC is therefore different from the physical volume (PCC) which is the actual physical displacement within the unit as determined by the unit's geometry.

The physical volume of the lower manifold system is $$V_{SL-B} = V_L + V_B$$
$$= 17.7 + 1016.0$$
$$= 1033.7 \text{ PCC.}$$

The volumetric quantities of gases contained in the physical volume is determined as follows:

$$T_{L-B} = \frac{T_L + T_B}{2}$$

$$= \frac{536.7 + 536.7}{2}$$

$$= 536.7° \text{ R.}$$

Since $$V_{SL-B} = V_{SL-B} \frac{(491.7)}{(T_{SL-B})} \frac{(P_{FL-B})}{(760)}$$

-continued
$$= 1033.7 \frac{(491.7)}{(536.7)} \frac{(410.0)}{(760.0)}$$

$$= 510.90 \text{ SCC.}$$

(2) Next the volumetric quantity of reference gas contained in the lower manifold system is determined. For the field evaluation being considered, this quantity will be approximated by calculating the total quantity (in SCC) reference gas contained in the system just prior to the initial equalization, step 20. (In the more exact case, part 2, the gas contained in the sample both will be spectrographically equalized and the exact quantities of the reference gas will be known).

The volumetric quantity of reference gas $V_{RU}$ in the upper manifold is $$V_{RU} = V_U \left( \frac{491.7}{T_U} \right) \left( \frac{P_{U_1}}{760} \right)$$

Since the physical volume of $V_U$ is known to be 16.4 PCC $$= 16.4 \left( \frac{491.7}{536.7} \right) \left( \frac{812.33}{760.0} \right)$$

$$= 16.06 \text{ SCC.}$$

The volumetric quantity of reference gas in the lower manifold system is $$V_{RL-R} = V_{SL-B} \left( \frac{491.7}{T_{SL-B}} \right) \left( \frac{P_{IL-B}}{760.0} \right)$$

$$= 1033.7 \left( \frac{491.7}{536.7} \right) \left( \frac{3.5}{760} \right)$$

$$= 4.36 \text{ SCC.}$$

The total volumetric quantity of reference gas, $V_{RT}$, is $$V_{RT} = V_{RU} + V_{RL-B}$$
$$= 16.06 + 4.36$$
$$= 20.42 \text{ SCC.}$$

The volumetric quantity of gas, in the lower manifold which originated from the electronic device and that has passed through the Drager Tube, $V_{EL-B}$ is the difference between the total volumetric quantity calculated in 1 less the volumetric quantity of reference gas calculated in 2, or $$V_{EL-B} = V_{GL-B} - V_{RT}$$
$$= 510.90 - 20.42$$
$$= 490.48 \text{ SCC.}$$

(3) As the above calculated volumetric quantity of gas passes through the Drager Tube, any moisture, in the form of water vapor, is removed from the gas and collected on the reactant surfaces on the material contained in the Drager Tube. Since the tube provides a direct quantitative reading the result of the moisture collected, $W_{H2O}$, is known (Drager Tube reading) and convertible to an equivalent volumetric quantity.

$$W_{H2O} = 20.5 \text{ mg.}$$
$$= 0.0205 \text{ gms.}$$

This quantity may be converted to gram moles, $M_{H2O}$, by dividing by its molecular weight ($M_W$).

$$M_{H2O} = \frac{W_{H2O}}{M_w}$$

$$= \frac{.0205}{18}$$

$$= 1.138 (10^{-3}) \text{ gm. moles.}$$

Since a mole of any substance, when converted to a gas, occupies the volumetric quantity of 22,414 SCC, the volumetric quantity of water vapor, $V_{H2O}$ absorbed is $$V_{H2O} = 1.138 (10^{-3}) (22414)$$
$$= 25.53 \text{ SCC.}$$

(4) The total volumetric quantity of gas which entered the Drager Tube, $V_{GDT}$ is therefore $$V_{GDT} = V_{EL-B} + V_{H2OV}$$
$$= 490.48 + 25.53$$
$$= 516.01 \text{ SCC.}$$

The percent concentration of water vapor, % $H_2O$, in this gas is $$\% H_2O = \frac{V_{H2OV}}{V_{GDT}} (100)$$

$$= \frac{25.53}{516.01} (100)$$

$$= 4.95\%$$

To calculate the Dew Point, it is necessary to determine the partial pressure of water vapor $$P_{pH2O}$$

present in the electronic device. In our case:

$$P_{PH2O} = \frac{\% H_2O (P_E)}{100}$$

$$= \frac{(4.95)(930.63)}{100}$$

$$= 46.07 \text{ Torr.}$$

Using standard reference tables, the Dew Point is 98° F. (The Dew Point is a convenient method to describe the moisture content of the device as it is the temperature where water vapor will condense from the gaseous mixture as a liquid.)

Determination of Device Internal Volume

The total weight of the gas leaving electronic equipment enclosure must be determined. The value is the sum of the weights of the gases (from the device) in the lower and upper manifolds plus the weight of water vapor absorbed in the Drager Tube.

The weight of gases from the device in the lower manifold is determined from the values calculated in the above section and an assumed molecular weight, ($M_G$) for the gaseous mixture in the lower manifold system.

Assuming $M_G$ to be 28.0, the weight in the lower system ($W_{gDT}$)

$$= \frac{V_{EL-B}}{22414} \frac{M_g}{453.9}$$

$$= 1.351 (10^{-3}) \text{ lbs.,}$$

and the weight of water absorbed by from the Drager Tube ($W_{WDT}$)

$$= 20.5 \text{ mgs.}$$
$$= 0.0205 \text{ gms./453.6 (gms./lb.)}$$
$$= 0.0452 (10^{-3}) \text{ lbs.}$$

Since the gas in the upper manifold is approximately 5% water vapor, the average molecular weight of the gas, $M_E$, in the upper manifold (and the electronic device) is $$M_E = (\% \text{ gas}) M_G + (\% H_2O) M_{water}$$

$$= \frac{(100 - 4.95)(28) + 4.95(18)}{100}$$

$$= 26.89$$

Using formula 16, the free void value in the electronic enclosure is 998.06 cc. This indicates that the internal seals are intact.

PART 2

Final Results (After composition of gas sample is known)

The only difference between the preliminary analysis and the final analysis is the estimation of the average gas molecular weight in the lower assembly following final equalization.

(In Part 1, this value is estimated from past data, while in Part 2, the value is known from spectrographic analysis.)

Based on the results of a mass spectrographic analysis (see Table 2), the average molecular weight of the gas in the test unit is computed by normalizing the measured results to remove the argon constituent introduced as the reference gas. Table 3 summarizes the calculations.

TABLE 2

| Mass Spectrometry Test Results | |
|---|---|
| | Mole Percent |
| Hydrogen | 0.003 |
| Helium | 1.024 |
| Methane | 0.002 |
| Nitrogen | 76.245 |
| Oxygen | 18.793 |
| Argon | 3.819 |
| Hydrocarbons as butane | 0.002 |
| Carbon dioxide | 0.104 |
| Water | .008 |

TABLE 3

FINAL MAGS TEST RESULTS
Analysis of Gases from
a Typical Electronic Enclosure
(Conditioned at 75° C. for greater than 20 hours)
Test Date 11/12/79

| SPECIE | "AS RECEIVED" MOLE PERCENT | NORMALIZED TO REMOVE ARGON MOLE PERCENT | NORMALIZED TO INCLUDE DRAGER WATER MOLE PERCENT |
|---|---|---|---|
| $H_2$ | 0.003 | 0.003 | 0.003 |
| He | 1.024 | 1.064 | 1.012 |
| Methane | 0.002 | 0.002 | 0.002 |
| Water | 0.008 | 0.008 | 4.947 |
| $N_2$ | 76.243 | 79.272 | 75.355 |
| $O_2$ | 18.792 | 19.538 | 18.573 |
| A | 3.819 | — | — |
| Hydrocarbon ($C_4$) | 0.002 | 0.002 | 0.001 |
| Carbon Dioxide | 0.104 | 0.108 | 0.103 |
| Trichloroethane | 0.003 | 0.003 | 0.003 |
| TOTAL | 100.00 | 100.00 | 100.00 |
| Molecular weight | 28.98 | 28.55 | 28.02 |

The finalized data is presented in Table 4 together with a comparison vis-a-vis preliminary estimates determined on-site.

TABLE 4

FINAL RESULTS AND COMPARISON WITH PRELIMINARY ESTIMATE

| | Units | Preliminary | Final |
|---|---|---|---|
| Pressure | Inch Hg | 36.6 | 36.6 |
| Moisture Content | % | 4.95 | 4.95 |
| Device Volume | cc | 998.60 | 978.60 |

Final Conclusion as to the Acceptability of the Unit

It is evident that the unit has experienced a failure in the primary atmospheric seal. In the field evaluation this is indicated by
(1) The loss of pressure
(2) High moisture content
(3) No change in internal volume (found to be in the order of 1000 cc instead of 1200 cc which would be the indicated value if the internal seals failed)

The conclusion is further verified in the final part 2 analysis, which shows a high concentration of oxygen in the collected gases, (none was present originally), while the initial 10% Helium concentration has been drastically reduced.

I claim:

1. A test system for detecting a contaminant in a pressurant gas within the free internal space of an enclosure, said enclosure having a gas coupling and an externally operable valve for controlling gas admission and removal, comprising: a coupling device for mating to said enclosure gas coupling and having manual means for actuating said enclosure externally operable valve; a colometric detector tube comprising an elongated column of granular material subject to color change for visual qualitative and quantitative indication of said contaminant when gas containing said contaminant is passed through said detector tube; a vacuum source, a sample vessel and an interconnection system of gas-tight tubing and valves arranged to evacuate at least partially said coupling device, said detector tube, said sample vessel and said inter connection system when a predetermined setting of said valves is extant, said gas within said enclosure being at least partially withdrawn through said detector tube when a second predetermined combination of settings of said valves is extant, the amount of said contaminant drawn through said detector tube being indicated by the length of the color-changed portion of said column of material in said detector tube.

2. A system according to claim 1 in which said contaminant is water vapor, said detector tube is a Drager tube and said contaminant indicating material is water responsive.

3. Apparatus according to claim 1 further including a supply of reference gas and at least one first additional valve in series therewith connecting into said system, said valves and said first additional valve being adjustable in a third predetermined combination to admit said reference gas into said system and said enclosure after said system and enclosure evacuation.

4. A system according to claim 1 further including a supply of pressurant gas and at least one second additional valve in series therewith connecting into said system, said valves and said second additional valves being adjustable in a fourth predetermined combination to recharge said enclosure with said pressurant gas.

5. A system according to claim 3 further including a supply of pressurant gas and at least one second additional valve in series therewith connecting into said system, said valves and said second additional valves being adjustable in a fourth predetermined combination to recharge said enclosure with said pressurant gas.

6. A system according to claim 5 in which said contaminant is water vapor, said detector tube is a Drager tube and said contaminant indicating material is water responsive.

7. A system according to claim 1 in which first and second manifolds are included in said system adjacent to first and second ends of said detector tube, respectively, in which corresponding first and second absolute pressure gauges are discretely connected to said manifolds, and in which temperature measuring devices are located to measure temperatures at said manifolds, at said enclosure and at said sample vessel, the pressure and temperature reading obtained during use of said system being available for subsequent calculation of masses and volume of gas and contaminant in said system and said enclosure.

8. A system according to claim 1 in which said coupling device includes an impedance device for limiting the rate of gas flow between said enclosure and said system.

9. A system according to claim 7 in which said coupling device includes an impedance device for limiting the rate of gas flow between said enclosure and said system.

10. A system according to claim 1 in which said sample vessel is defined as having a volume substantially larger than the sum of the volumes of said enclosure and said test system, and in which the interconnection between said coupling device and said test system is a capillary tube to minimize its contribution to the test system volume.

11. A system according to claim 7 in which said sample vessel is defined as having a volume substantially larger than the sum of the volumes of said enclosure and said test system, and in which the interconnection between said coupling device and said test system is a capillary tube to minimize its contribution to the test system volume.

* * * * *